US009827211B2

(12) United States Patent
Ravenelle et al.

(10) Patent No.: US 9,827,211 B2
(45) Date of Patent: Nov. 28, 2017

(54) USES AND METHODS FOR THE TREATMENT OF LIVER DISEASES OR CONDITIONS

(71) Applicant: Verlyx Pharma Inc., Montreal, Quebec (CA)

(72) Inventors: Francois Ravenelle, Montreal (CA); Pierre Falardeau, Westmount (CA); Patrick Colin, St-Bruno de Montarville (CA)

(73) Assignee: Verlyx Pharma Inc., Montreal, Quebec (CA)

( * ) Notice: Subject to any disclaimer, the term of this patent is extended or adjusted under 35 U.S.C. 154(b) by 0 days.

(21) Appl. No.: 15/178,301

(22) Filed: Jun. 9, 2016

(65) Prior Publication Data

US 2016/0287535 A1 Oct. 6, 2016

Related U.S. Application Data

(63) Continuation of application No. 14/653,807, filed as application No. PCT/CA2013/051003 on Dec. 20, 2013, now Pat. No. 9,375,411.

(60) Provisional application No. 61/745,011, filed on Dec. 21, 2012.

(51) Int. Cl.
*A61K 31/155* (2006.01)
*A61K 9/20* (2006.01)
*A61K 9/48* (2006.01)
*A61K 45/06* (2006.01)
*A61K 31/10* (2006.01)
*A61K 9/00* (2006.01)
*A61K 31/185* (2006.01)

(52) U.S. Cl.
CPC .......... *A61K 31/155* (2013.01); *A61K 9/0053* (2013.01); *A61K 9/20* (2013.01); *A61K 9/48* (2013.01); *A61K 31/10* (2013.01); *A61K 31/185* (2013.01); *A61K 45/06* (2013.01)

(58) Field of Classification Search
None
See application file for complete search history.

(56) References Cited

U.S. PATENT DOCUMENTS

| 4,853,416 | A | 8/1989 | Anaebonam et al. |
| 5,084,480 | A | 1/1992 | Pai et al. |
| 5,162,361 | A | 11/1992 | Rosenthal et al. |
| 5,204,113 | A | 4/1993 | Hartley et al. |
| 5,786,383 | A | 7/1998 | Clement |
| 6,569,853 | B1 | 5/2003 | Borisy et al. |
| 6,693,125 | B2 | 2/2004 | Borisy et al. |
| 7,037,917 | B2 | 5/2006 | De Corte et al. |
| 7,115,665 | B1 | 10/2006 | Chow et al. |
| 7,148,216 | B2 | 12/2006 | Borisy et al. |
| 7,884,090 | B2 | 2/2011 | Bonner, Jr. et al. |
| 7,947,741 | B2 | 5/2011 | Bostian et al. |
| 7,993,639 | B2 | 8/2011 | Yi |
| 7,994,225 | B2 | 8/2011 | Bostian et al. |
| 8,436,049 | B2 | 5/2013 | Berglund et al. |
| 2004/0010045 | A1 | 1/2004 | Yi |
| 2005/0054708 | A1 | 3/2005 | Nichols et al. |
| 2006/0122279 | A1 | 6/2006 | Burns et al. |
| 2006/0235001 | A1 | 10/2006 | Elliott et al. |
| 2007/0093424 | A1 | 4/2007 | Burns et al. |
| 2007/0197658 | A1 | 8/2007 | David et al. |
| 2007/0232674 | A1 | 10/2007 | Burns et al. |
| 2008/0226596 | A1 | 9/2008 | Yi |
| 2010/0323993 | A1 | 12/2010 | Berglund et al. |
| 2012/0128667 | A1 | 5/2012 | Chow et al. |
| 2012/0277193 | A1 | 11/2012 | Roth et al. |
| 2013/0244963 | A1 | 9/2013 | Sinha et al. |

FOREIGN PATENT DOCUMENTS

| DE | 2833135 | 2/1980 |
| DE | 4321444 A1 | 1/1995 |
| EP | 2550963 | 1/2013 |
| GB | 1288376 | 9/1972 |
| JP | H08333324 | 12/1996 |
| JP | H0975446 | 3/1997 |
| WO | WO 02/058684 | 8/2002 |
| WO | WO 2009/954599 | 8/2009 |

OTHER PUBLICATIONS

Adbi et al., Handbook of drugs for tropical parasitic infections, p. 117-122, 1995.
Blaschko et al., The inhibition of amine oxidase by amidines, Biochem J., vol. 39, p. 347-350, 1945.
Clement et al., Diacetyldiamidoximeester pf pentamidine, a prodrug for treatment of protozoal diseases: synthesis, in vitro and in vivo biotransformation, ChemMedChem, p. 1260-1267, 2006.
David et al., Biophysical mechanisms of the neutralization of endotoxins by Lipopolyamines, The Open Biochemistry Journal, vol. 7, p. 82-93, 2013.
David et al., Interaction of cationic amphiphilic drugs with lipid A: Implications for development of endotoxin antagonists, Biochimica et Biophysica Acta 1212, p. 167-175, 1994.
Fenton et al., LPS-binding proteins and receptors, Journal of Leukocyte Biology, vol. 64, p. 25-32, 1998.
Kotthaus et al., New prodrugs of the antiprotozoal drug pentamidine, ChemMedChem, vol. 6, p. 2233-2242, 2011.
Kotthaus et al., Synthesis and biological evaluation of L-valine-amidoximeesters as double prodrugs of amidines, Bioorganic & Medicinal Chemistry 19, p. 1907-1914, 2011.
Libman et al., Antistaphylococcal activity of pentamidine, Antimicrobial Agents and Chemotherapy, vol. 34, No. 9, p. 1795-1796, 1990.
Lourie, E.M., The blood-brain barrier and cerebrospinal fluid in relation to the efficacy of sleeping-sickness drugs, Trans. Faraday Soc., vol. 39, p. 340-347, 1943.

(Continued)

*Primary Examiner* — Brian J Davis
(74) *Attorney, Agent, or Firm* — Edward J. Baba; Bozicevic, Field & Francis LLP

(57) ABSTRACT

The present application relates methods and uses of oral diamidines or pharmaceutically acceptable salts thereof for the treatment of liver diseases or conditions.

17 Claims, 8 Drawing Sheets

(56) References Cited

OTHER PUBLICATIONS

Masur, Henry, Prevention and treatment of pneumocystis pneumonia, Drug Therapy, The New England Journal of Medicine, vol. 327, No. 26, p. 1853-1860, 1992.
Mdachi et al., Efficacy of the Novel Diamidine Compound 2,5-Bis(4-Amidinophenyl)-Furan-Bis-O-Methlylamidoxime (Pafuramidine, DB289) against Trypanosoma brucei rhodesiense Infection in Vervet Monkeys after Oral Administration, Antimicrob. Agents Chemother, 53(3), p. 953-957, 2009.
Parker et al., The inhibitory effects of pentamidine on biochemical events in human liver cells, Toxicol In Vitro., Vo.7, No. 2, p. 177-184, 1993.
Pathak et al., Pentamidine is an inhibitor of PRL phosphatases with anticancer activity, Molecular Cancer Therapeutics, vol. 1, p. 1255-1264, 2002.
Purfield et al., The diamidine DB75 targets the nucleus of Plasmodium falciparum, Malaria Journal, 2009, 8:1.04, p. 1-9.
Reynolds et al., Pentadimine is an N-methyl-D-aspartate receptor antagonist and is neuroprotective in vitro, The Journal of Neuroscience, vol. 12, No. 3, p. 970-975, 1992.
Rosenthal et al., Pentadimine blocks the pathophysiologic effects of endotoxemia through inhibition of cytokine release, Toxicology and applied pharmacology 112, p. 222-228, 1992.
Shrestha, Anurupa, Design, Syntheses, and Evaluation of Lipopolyamines as Anti-Endotoxin Agents, Submitted to the Department of Medicinal Chemistry and the Faculty of the Gradute School of the University of Kansas, p. 23-35, 2007.
Sieve et al., Pentamidine, Journal of Pediatric Oncology Nursing, vol. 11, No. 2, p. 85-87, 1994.
Sippel et al., Influence of pentamidine and two new trypanocidal agents (DAPI, DIPI) on liver metabolism of mice, Pharmacol Toxicol, vol. 69, No. 5, p. 372-377, 1991.
Smith et al., The effect of pentamidine on melanoma ex vivo, Anticancer Drugs, vol. 21, No. 2, p. 181-185, 2010.
Tidwell et al., Activity of cationically substituted bis-benzimidazoles against experimental Pneumocystis carinii pneumonia, Antimicrob. Agents Chemother. 37(8), p. 1713-1716, 1993.
Bernard, E. M.; Donnelly, H. J.; Maher, M. P.; Armstrong, D.; "Use of a New Bioassay to Study Pentamidine Pharmacokinetics"; Journal of Infectious Diseases; Oct. 1985; vol. 152, No. 4; pp. 750-754.
Bronner, U.; Ericsson, Ö.; Nordin, J.; Wikström, I.; Abdi, Y. A.; Hall, J. E. et al.: "Metabolism is an Important Route of Pentamidine Elimination in the Rat: Disposition of 14C-Pentamidine and Identification of Metabolites in Urine Using Liquid Chromatography—Tandem Mass Spectrometry"; Pharmacology & Toxicology; 1995; vol. 77; pp. 114-120.
Clement, B., Immel, M., Terlinden, R. & Wingen, F.-J.; "Reduction of Amidoxime Derivatives to Pentamidine in vivo"; Arch. Pharm. (Weinheim); 1992; vol. 325; pp. 61-62.
Donnelly, H., Bernard, E. M., Rothkotter, H., Gold, J. W. M. & Armstrong, D.; "Distribution of Pentamidine in Patients with AIDS"; Journal of Infectious Diseases; 1988; vol. 157; pp. 985-989.
Glaumann, H., Bronner, U., Ericsson, Ö., Gustafsson, L. L. & Rombo, L.; "Pentamidine Accumulates in Rat Liver Lysosomes and Inhibits Phospholipid Degradation"; Pharmacology & Toxicology; 1994; vol. 74; pp. 17-22.
Terlinden, R. & Römer, A.; "Pharmacokinetics and toxicokinetics of pentamidine in the rat following intravenous and aerosol administration" (abstract only); Med. Klin. (Munich); 1990; vol. 85, No. 2; pp. 245-247.
Thomas, S. H. et al.; "Disposition of intravenous 123iodopentamidine in man"; Nuclear Medicine and Biology; 1997; vol. 24; pp. 327-332.
Waalkes, T. P., Denham, C. & DeVita, V. T.; "Pentamidine: Clinical pharmacologic correlations in man and mice"; Clinical Pharmacology and Therapeutics; 1970; vol. 11; pp. 505-512.
Waalkes, T. P. & Makulu, D. R.; "Pharmacologic aspects of pentamidine" (abstract only); Natl. Cancer Inst. Monogr.; 1976; vol. 43; pp. 171-177.
Wingen, F. & Brägas, B.; "Autoradiographic examination of the organ distribution of 14C-labelled pentamidine in rats after intravenous and inhaled administration" (abstract only); Arzneimittelforschung; 1991; vol. 41, No. 9; pp. 937-945.
Berger, B.J. et al.; "The Distribution of Multiple Doses of Pentamidine in Rats"; Pharmacology& Toxicology; 1990; pp. 234-236.

USES AND METHODS FOR THE TREATMENT OF LIVER DISEASES OR CONDITIONS

CROSS-REFERENCE TO RELATED APPLICATIONS

This application is a continuation of U.S. patent application Ser. No. 14/653,807 filed on Jun. 18, 2015, which is a 371 of PCT/CA2013/051003 filed on Dec. 20, 2013, which claims priority to U.S. Provisional Patent Application Ser. No. 61/745,011 filed on Dec. 21, 2012, the disclosures of which are incorporated herein by reference in their entirety.

The present application relates to uses, methods and pharmaceutical composition for the treatment of liver diseases or conditions.

Pentamidine is approved for parenteral administration (intravenous and inhalation) as an anti-protozoal agent. Parenteral (intravenous) pentamidine is also currently being developed for lung cancer, pancreatic cancer and colon cancer.

Based on scientific literature, it is well accepted that pentamidine is not suitable for oral administration due to its poor absorption (Sieve et al.: *JOPON*, Vol. 11, Vol. 2 (April) 1994: pp 85-87; Masur H: *N. Eng J. Med.* 327: 1853-1860 (1992); Abdi et al. *Handbook of Drugs for tropical parasitic Infections* ISBN0-7484-0168-7; pp 117-122).

It is however desirable to give oral forms to patients. Advantages associated with oral forms include higher patient compliance and ease of administration.

In one aspect, there is provided, a method for the targeted treatment of one or more liver conditions comprising the step of orally administering a therapeutically effective amount of at least one diamidine analogue or a pharmaceutically acceptable salt thereof to a human patient in need thereof; wherein the liver condition is liver cancer, liver metastasis, high cholesterol, alcoholic liver disease, cirrhosis, cysts, fatty liver disease (NAFLD), fibrosis, jaundice, primary sclerosing cholangitis (PSC), hemochromatosis, primary biliary cirrhosis or Alpha-1 Antitrypsin Deficiency.

In one aspect, there is provided, the oral use of a therapeutically effective amount of at least one diamidine analogue or a pharmaceutically acceptable salt thereof for the targeted treatment of one or more liver conditions in a human patient in need thereof; wherein the liver condition is liver cancer, liver metastasis, high cholesterol, alcoholic liver disease, cirrhosis, cysts, fatty liver disease (NAFLD), fibrosis, jaundice, primary sclerosing cholangitis (PSC), hemochromatosis, primary biliary cirrhosis or Alpha-1 Antitrypsin Deficiency.

Figure 1:
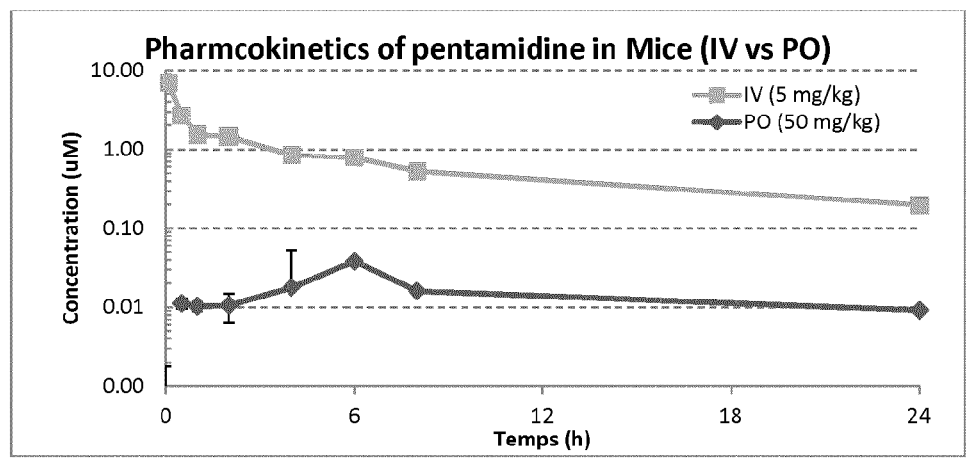
FIG. 1 represents the pharmcokinetics of pentamidine in Mice (IV vs PO).

Applicant has found that oral administration of diamidines (e.g., pentamidine) (vs the usual parenteral one) distribute preferentially in the liver.

Applicant has found that oral administration of diamidines (e.g., pentamidine) (vs the usual parenteral one) distribute preferentially in the liver at therapeutic concentrations.

Oral administration refers to administration of the diamidine analogue by mouth. In one aspect the diamidine analogue is swallowed by the patient. Oral administration include the administration of a tablet, a capsule, an elixir, or a solution or other liquid form of the diamidine analogue by mouth. In one aspect, oral administration also include buccal (dissolved inside the cheek), sublabial (dissolved under the lip) and sublingual administration (dissolved under the tongue).

In one embodiment, the level of diamidines (e.g., pentamidine) is increased in the liver of the patient relative to the diamidines (e.g., pentamidine) level in other tissues and organs.

In one embodiment there is provided, the use of a therapeutically effective amount of at least one diamidine analogue (e.g., pentamidine) or a pharmaceutically acceptable salt thereof in oral form to selectively deliver at least one diamidine analogue (e.g., pentamidine) to the liver of a patient suffering from one or more liver conditions or diseases.

In one embodiment there is provided, a method to selectively deliver at least one diamidine analogue (e.g., pentamidine) to the liver of a patient suffering from one or more liver conditions or diseases comprising orally administering a therapeutically effective amount of at least one diamidine analogue (e.g., pentamidine) or a pharmaceutically acceptable salt thereof.

In one embodiment there is provided, a method to reduced or prevent liver damage comprising orally administering a therapeutically effective amount at least one diamidine analogue (e.g., pentamidine) or a pharmaceutically acceptable salt thereof to a patient in need thereof.

Treatment of Liver Cancer and Liver Metastases

Since diamidines (e.g., pentamidine) preferentially accumulate in the liver in therapeutic concentrations following oral administration, they could be used orally for the treatment liver cancer or liver metastasis.

In one aspect, the liver cancer is intrahepatic bile duct cancer or hepatocarcinoma.

In one aspect, the liver metastasis is liver dominant cancer metastasis or liver limited cancer metastasis.

In oncology, most metastasis occurs in the liver, a vital organ. Rapidly, the primary cancer that has metastasized in the liver becomes life-threatening. For this reason, it is desirable to target the delivery of anti-cancer agents directly to the liver. Because many anti-cancer drugs may have secondary effects, toxicity related to their action on healthy cells elsewhere in the body, it is desirable to have a targeted delivery of anti-cancer agents to the liver. In one embodiment there is provided, the oral use of a therapeutically effective amount of at least one diamidine analogue (e.g. pentamidine) or a pharmaceutically acceptable salt thereof for the targeted treatment liver metastasis, liver dominant cancer metastasis or liver limited cancer metastasis in a patient in need thereof or having received a diagnosis of liver metastasis, liver dominant cancer metastasis or liver limited cancer metastasis.

In one embodiment there is provided, the uses or methods as defined herein, for treating liver dominant colorectal cancer metastasis.

Liver dominant cancer metastasis refers to metastases that are mainly located in the liver (e.g., determination of size, number and type of lesions).

Liver limited cancer metastasis refers to metastases that are only located in the liver (e.g., determination of size, number and type of lesions).

In one aspect, the cancer condition or status of the patient is determined in accordance with the Response Evaluation Criteria in Solid Tumours (RECIST). See for example EUROPEAN JOURNAL OF CANCER 45 (2009) 228-247

In one embodiment there is provided, the uses or methods as defined herein, for treating metastasized cancer.

In one aspect, the patient has one or more of the following conditions:
  a. Inoperable liver tumors, minor lung or bone metastasis or abnormal hepatic enzyme level.

In one embodiment there is provided, the uses or methods as defined herein, wherein the primary cancer originates from squamous cell carcinoma cells, larger cell carcinoma of the lymph node cells, breast cancer cells, colon cancer cells, lung carcinoma cells, melanoma cells, pancreatic cancer cells, leukemia cells, non-small cell lung cancer cells, colon cancer cells, central nervous system (CNS) cancer cells, ovarian cancer cells, renal cancer cells or prostate cancer cells.

In one aspect, the cancer patient is treated as long as the disease is stable or until there is tumor progression (e.g., diseases progression, appearance of new lesions etc.).

In one embodiment there is provided, the use or method of as defined herein wherein the primary cancer originates from pancreatic cancer cells, colon cancer cells, breast cancer cells or ovarian cancer cells.

In one embodiment the diamidine analogues (e.g., pentamidine) are used in combination with standard chemotherapy.

In one embodiment there is provided, an oral pharmaceutical composition comprising at least one diamidine analogue (e.g., pentamidine) or a pharmaceutically acceptable salt thereof and one or more further therapeutic agent indicated for the treatment of cancer.

In one embodiment there is provided, an oral pharmaceutical composition comprising at least one diamidine analogue (e.g., pentamidine) or a pharmaceutically acceptable salt thereof and one or more further therapeutic agent for inhibiting the proliferation of cancer cells or for the treatment of cancer.

Other Liver Conditions or Diseases

Since diamidines (e.g., pentamidine) preferentially accumulate in the liver following oral administration, they could also be used for the treatment of other conditions associated with the liver. In one embodiment, the liver condition is high cholesterol, alcoholic liver disease (including acute alcoholic hepatitis), cirrhosis, cysts, primary biliary cirrhosis, fatty liver disease (NAFLD), fibrosis, jaundice, primary sclerosing cholangitis (PSC), hemochromatosis, primary biliary cirrhosis, or Alpha-1 Antitrypsin Deficiency. See http://www.rightdiagnosis.com/l/liver/basics.htm for liver conditions.

In one aspect, liver damage is determined by standard liver function tests and or by imaging (CT, X-Ray, MRI etc.). Liver function tests include bilirubin, ammonia, gamma-glutamyl transferase (GGT), alanine aminotransferase (ALT or SGPT), aspartate aminotransferase (AST or SGOT), and alkaline phosphatase (ALP).

In one aspect, in the use or method of as defined herein, the patient is not seeking treatment for a viral hepatitis (e.g., A, B, C, D, E or G).

Non-Alcoholic Fatty Liver Disease (NAFLD) and Non-Alcoholic Steatohepatitis (NASH)

NAFLD and its more severe form NASH are associated with several diseases (obesity, type 2 diabetes, dyslipidaemia and hypertension), having insulin resistance as the common factor. These conditions cluster to form the insulin resistance or metabolic syndrome, carrying a high risk for cardiovascular complications. NASH itself, as well as pure fatty liver, is an insulin-resistant state, not only in subjects with additional metabolic disorders, but also in lean subjects.

Because the histopathology of NASH resembles that of alcohol-induced steatohepatitis (ASH), these 2 conditions share common pathogenic aspects. Immunological mechanisms play a pivotal role in the pathogenesis of ASH. This has been well demonstrated by studies of patients and experimental animals. In hospitalized patients with severe ASH and NASH, serum levels of several pro-inflammatory cytokines, including TNF-α, are increased significantly. Cytokine levels correlate well with liver disease severity.

While it is widely acknowledged that TNF-α expression increases in obesity, the mechanisms driving chronic over-production of TNF-α in obese humans remain obscure. However, the resultant chronic inflammatory state has been implicated in the pathogenesis of the metabolic syndrome that often accompanies obesity. The immunopathogenesis of obesity-related NASH has been studied extensively in the ob/ob mice model. The studies clearly demonstrate that cytokine producing cells in ob/ob livers are Th1 polarized. This microenvironment favours the perpetuation of inflammatory signals. Inhibiting TNFα significantly reduced the hepatic activities of both kinases, thereby supporting the concept that excessive TNFα activity contributes to hepatic insulin resistance in leptin-deficient mice. A strong positive correlation has been noted between hepatic insulin resistance and NASH in many experimental animals and humans.

NAFLD and NASH are initially suspected if blood tests show high levels of liver enzymes. An ultrasound is typically used to confirm the NAFLD diagnosis.

In one aspect, in the uses and methods as described herein the NASH or NAFLD patient will be treated orally with the diamidine analogue in order to prevent, control or reduce liver damage.

In one aspect, in the uses and methods as described herein the patient is a NASH or NAFLD patient that has developed cirrhosis.

In one aspect, in the uses and methods as described herein the NASH or NAFLD patient is overweight or obese, has diabetes, high cholesterol or high triglycerides.

High Cholesterol

High blood cholesterol levels are associated with increased risk of suffering from heart attack and stroke.

In one aspect, the patient is a patient having elevated blood cholesterol levels.

In one aspect, an elevated cholesterol level is a total blood cholesterol level that exceeds 200 mg/dL, that exceeds 220 mg/dL or that exceeds 240 mg/dL.

In one aspect, in the uses and methods as described herein, the patient will be treated orally with the diamidine analogue in order reduce or maintain the total blood cholesterol level below 200 mg/dL, below 220 mg/dL or below 240 mg/dL.

Alcoholic Liver Disease (ALD)

Alcoholic liver disease occurs after years of heavy drinking. Alcohol can cause inflammation in the liver. ALD has three stages: 1) alcoholic fatty liver disease; 2) alcoholic hepatitis and 3) Cirrhosis.

Alcoholic hepatitis (not related to infectious hepatitis) is the second, more serious stage of ALD. It occurs when alcohol misuse over a longer period causes the tissues of the liver to become inflamed.

Damage caused by alcoholic fatty liver disease or Alcoholic hepatitis can usually be reversed if the use of alcohol is stopped.

Cirrhosis is the final stage of alcohol-related liver disease, which occurs when the liver becomes significantly scarred. Cirrhosis is generally not reversible, but stopping drinking alcohol can prevent further damage and significantly increase life expectancy.

In one aspect the ALD is diagnosed with blood test, liver biopsy or imagery (ultrasound scan, computerised tomography (CT) scan).

In one aspect, in the uses and methods as described herein the ALD patient will be treated orally with the diamidine analogue in order to prevent, control or reduce liver damage.

Cirrhosis

Cirrhosis is scarring of the liver caused by many forms of liver diseases and conditions, such as hepatitis and chronic alcohol abuse.

In one aspect the ALD is diagnosed with blood test, liver biopsy or imagery (ultrasound scan, computerised tomography (CT) scan).

In one aspect, in the uses and methods as described herein the cirrhosis patient will be treated orally with the diamidine analogue in order to prevent, control or reduce liver damage.

Cysts

Cysts are thin-walled structures that contain fluid. Most cysts are single, although some patients may have several. The symptoms associated with liver cysts include upper abdominal fullness, discomfort, or pain.

The cysts are usually found by ultrasound (US) or computed tomography (CT scan).

In one aspect, in the uses and methods as described herein the cysts patient will be treated orally with the diamidine analogue in order to prevent, control or reduce the cysts and/or the symptoms associated with liver cysts.

Fibrosis

Liver fibrosis is the scarring process that represents the liver's response to injury.

Liver fibrosis is usually found by biopsy.

In one aspect, in the uses and methods as described herein the liver fibrosis patient will be treated orally with the diamidine analogue in order to prevent, reduce or control liver fibrosis or inflammation associated/caused by liver fibrosis.

Intra-Hepatic or Post-Hepatic Jaundice

There are three types of jaundice depending on what is causing disruption to the normal removal of bilirubin from the body.

In one aspect, in the uses and methods as described herein the jaundice patient is a patient that suffers from:
 a. intra-hepatic jaundice (also known as hepatocellular jaundice)—the disruption occurs inside the liver. This can be caused by conditions such as Gilbert's syndrome, cirrhosis or other liver damage.
 b. post-hepatic jaundice (also known as obstructive jaundice)—the disruption prevents the bile (and the bilirubin inside it) from draining out of the gallbladder and into the digestive system. This can be caused by conditions such as gallstones or tumours.

In one aspect, in the uses and methods as described herein the intra-hepatic or post-hepatic patient will be treated orally with the diamidine analogue in order to control, reduce or prevent liver damage.

In one aspect, in the uses and methods as described herein the jaundice patient suffers from intra-hepatic jaundice.

Primary Sclerosing Cholangitis (PSC)

PSC is a disease of the bile ducts. The term "cholangitis" in primary sclerosing cholangitis refers to inflammation of the bile ducts, while the term "sclerosing" describes the hardening and scarring of the bile ducts that result from chronic inflammation.

Primary sclerosing cholangitis is a progressive disease that leads to liver damage and, eventually, liver failure.

In one aspect, in the uses and methods as described herein the PSC patient will be treated orally with the diamidine analogue in order to reduce, control, or prevent liver damage.

Hemochromatosis

Hemochromatosis is an hereditary condition characterised in an excess on iron absorption. The excess iron is stored in organs, especially liver, heart and pancreas. The excess iron can poison these organs, leading to life-threatening conditions such as cancer, heart arrhythmias and cirrhosis.

In one aspect, in the uses and methods as described herein the PSC patient will be treated orally with the diamidine analogue in order to control, prevent or reduce liver damage.

Alpha-1 Antitrypsin Deficiency

The genetic defect in alpha1-antitrypsin (AAT) deficiency alters the configuration of the alpha1-antitrypsin molecule and prevents its release from hepatocytes. As a result, serum levels of alpha1-antitrypsin are decreased, leading to low alveolar concentrations, where the alpha1-antitrypsin molecule normally would serve as protection against antiproteases. The resulting protease excess in alveoli destroys alveolar walls and causes emphysema. The accumulation of excess alpha1-antitrypsin in hepatocytes can also lead to destruction of these cells and ultimately, clinical liver disease.

In one aspect, in the uses and methods as described herein the AAT patient will be treated orally with the diamidine analogue in order to prevent, control or reduce liver damage.

Primary Biliary Cirrhosis (PBC)

PBC is a slow, chronic liver disease which can cause progressive destruction of the bile ducts in the liver. The body attacks the cells lining the bile ducts within the liver as if they are foreign to the body itself. This damage causes poor drainage of bile acids, which leak outwards and damage the normal liver cells. This causes inflammation and scarring which may, after many years become extensive. This widespread damage and scarring is commonly called cirrhosis.

PBC usually diagnosed with blood tests. The presence of AMA (antimitochondrial antibody) is indicative of PBC.

In one aspect, in the uses and methods as described herein the PBC patient will be treated orally with the diamidine analogue in order to prevent, control or reduce liver damage.

In one aspect, in the uses and methods as described herein the PBC patient has tested positive for AMA.

Diamidines Analogues

In one aspect, the diamidine analogue is propamidine, butamidine, pentamidine, hexamidine, heptamidine, decamidine and so on, or stilbamidine, furamidine, pafuramidine, or 4,4'(diazoamino)dibenzamidine diaceturate.

In one aspect, the diamidine analogue is pentamidine.

Pentamidine refers to the free compound or to the compound in salt form, e.g., as the bis(2-hydroxyethanesulfonate) or isethionate salt, HCl, tosylate, mesylate, gluconate or any other pharmaceutically acceptable salt.

In one aspect, pentamidine refers to the free compound or to the compound in salt form, e.g., as the bis(2-hydroxyethanesulfonate) or isethionate salt, mesylate, gluconate or any other pharmaceutically acceptable salt.

Pentamidine is represented by the formula:

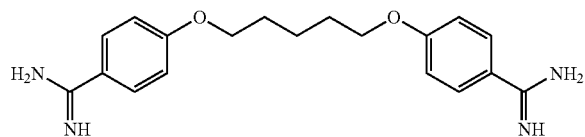 [SMILES: N=C(N)c1ccc(OCCCCCOc2ccc(C(=N)N)cc2)cc1]

In one embodiment, pentamidine is pentamidine bis(2-hydroxyethanesulfonate) or pentamidine isethionate.

Pentamidine is an antiprotozoal drug with additional antiinflammatory activities. It has been reported that pentamidine inhibited the human whole blood production of the chemotactic cytokines (chemokines) interleukin (IL)-8, growth related gene alpha (GRO alpha) and monocyte chemotactic protein-1 (MCP-1). The title compound dose-dependently suppress the lipopolysaccharide (LPS)- and phytohemagglutinin (PHA)-stimulated whole blood generation of these chemokines. The inhibition is specific: when tested at 10 microM, pentamidine has no significant inhibitory effect on the PHA-induced generation of the non-chemotactic cytokines tumor necrosis factor-alpha (TNF-alpha), IL-1 beta, IL-2, IL-4, IL-5, IL-10 and interferon-gamma (IFN-gamma), except for a partial inhibition on IL-6. These findings indicate that pentamidine is a post-transcription acting inhibitor of human chemokine production. This activity may contribute to the anti-inflammatory action ascribed to pentamidine.

Definitions

In one aspect, "selective" when referring to the delivery of pentamidine and "targeted" when referring to the treatment using oral pentamidine mean that the amount of pentamidine is increased in the liver of the patient relative to the amount of pentamidine in other tissues and organs (e.g. muscle, lung, kidney and heart) following oral administration if compared to distribution following intravenous administration. In a further aspect, the amount found in the liver is a therapeutically effective amount.

As used herein the term "patient" means human.

The term "therapeutically acceptable amount" refers to that amount of drug or pharmaceutical agent that will elicit the biological or medical response of a tissue, system or animal that is being sought be a researcher or clinician.

The term "treatment" (and corresponding terms "treat" and "treating") includes palliative, restorative, and preventative treatment of a patient.

The term "control liver damage" refers to treatment that eases or reduces the effect or intensity of a condition in a subject without curing the condition.

The term "prevent liver damage" (and the corresponding terms "prevention" and "prophylactic treatment") refers to treatment that prevents the occurrence of a condition in a patient.

The term "reduce liver damage" refers to treatment that halts the progression of or reduces the pathologic manifestations of a condition in a patient.

It is noted in that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers.

There is also provided pharmaceutically acceptable salts compounds recited herein. By the term pharmaceutically acceptable salts are meant those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, trifluoroacetic, citric, methanesulphonic, formic, benzoic, malonic, naphthalene-2-sulphonic and benzenesulphonic acids. Salts derived from amino acids are also included (e.g. L-arginine, L-Lysine).

Salts derived from appropriate bases include alkali metals (e.g. sodium, lithium, potassium) and alkaline earth metals (e.g. calcium, magnesium).

With regards to pharmaceutically acceptable salts, see also the list of FDA approved commercially marketed salts listed in Table I of Berge et al., Pharmaceutical Salts, J. of Phar. Sci., vol. 66, no. 1, January 1977, pp. 1-19.

It will be appreciated by those skilled in the art compounds can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will be appreciated that the amount of compounds required for use in treatment will vary not only with the particular compound selected but also with the route of administration, the nature of the condition for which treatment is required and the age and condition of the patient and will be ultimately at the discretion of the attendant physician.

The desired dose may conveniently be presented in a single dose or as divided dose administered at appropriate intervals, for example as two, three, four or more doses per day. While it is possible that, for use in therapy, the compounds may be administered as the raw chemical it is preferable to present the active ingredient as a pharmaceutical composition. The invention thus further provides a pharmaceutical combination or composition of the compounds as described herein or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

As used herein, the expression "an acceptable carrier" means a vehicle for the combinations and compounds described herein that can be administered to a subject without adverse effects. Suitable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like Pharmaceutical Composition of Diamidine Analogues In one embodiment there is provided, an oral pharmaceutical composition comprising at least one diamidine analogue (e.g., pentamidine) or a pharmaceutically acceptable salt thereof and one or more pharmaceutically acceptable carrier.

Pharmaceutical compositions of pentamidine include those suitable for oral administration. The compositions may, where appropriate, be conveniently presented in discrete dosage units and may be prepared by any of the methods well known in the art of pharmacy. All methods include the step of bringing into association the active with liquid carriers or finely divided solid carriers or both and then, if necessary, shaping the product into the desired composition.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. Pharmaceutical compositions include those suitable for oral administration. The compositions may, where appropriate, be conveniently presented in discrete dosage units and may be prepared by any of the methods well known in the art of pharmacy. All methods include the step of bringing into association the active with liquid carriers or finely divided solid carriers or both and then, if necessary, shaping the product into the desired corn position.

The diamidines can be conveniently administered in unit dosage form; for example containing 1 to 3000 mg, 1 to 2000 mg, 10 to 1500 mg, conveniently 20 to 1000 mg, most conveniently 50 to 700 mg of active ingredient per unit dosage form.

The diamidines can be conveniently administered at least every other day, once, twice or thrice daily. Depending on the treatment selected, the diamidines are administered consecutively for more than 15 days, more than 30 days or more than 45 days.

Typical daily IV doses of pentamidine are 2-8 mg/kg body weight in humans.

In one embodiment, the dose of pentamidine can be lower than the typical IV doses. Pentamidine can be conveniently administered in unit dosage form; for example containing 1 to 3000 mg, 1 to 2000 mg, 10 to 1500 mg, conveniently 20 to 1000 mg, most conveniently 50 to 700 mg of active ingredient per unit dosage form.

In one aspect, in the uses and methods described herein, the patient does not suffer from a fungal or protozoa infection (e.g., *Leishmania, Pneumocystis jiroveci (carinii)* or *Trypanosoma* infection), viral hepatitis (e.g., hepatitis A, B, B C, D, E or G), immune deficiency (HIV), pneumonia or multiple sclerosis.

Pharmaceutical Compositions of Further Therapeutic Agents when Used in Combination with Diamidine (for Sequential or Simultaneous Administration)

One embodiment of the invention includes method and uses thereof comprising a diamidine analogue (e.g., pentamidine) and at least one additional further agent indicated for the treatment of the liver condition.

One embodiment of the invention includes method and uses thereof comprising a diamidine analogue (e.g., pentamidine) in combination with standard therapy indicated for the treatment of the liver condition.

When the liver condition is liver cancer, standard therapy will include standard chemotherapy indicated for the type of cancer (e.g., standard of care).

One embodiment of the invention include method and uses thereof comprising pentamidine and at least one additional further anti-cancer agents for inhibiting the proliferation of cancer cells or for the treatment of cancer in a patient in need thereof.

In one embodiment the further agents include standard chemotherapy. By standard chemotherapy is meant chemotherapy regimen that are used for the treatment of the cancer to be treated.

In one embodiment the further agent include but are not limited to oxaliplatin, cisplatin, mitomycin C, melphalan, carmustine, adriamycin, paclitaxel, docetaxel, 5-fluorouracil, bevacizumab, cetuximab, capecitabine, folinic acid (also known as leucovorin), ionizing irradiation, bleomycin, carboplatin, irinotocan, and/or gemcitabine.

In a further embodiment, the further agent is carboplatin and/or gemcitabine.

In one embodiment the diamidine analogues (e.g., pentamidine) are used in combination with standard therapy indicated for the treatment of the liver condition.

In one embodiment the diamidine analogues (e.g., pentamidine) are not used in combination a cytokine or a granulocyte/macrophage stimulating factor (interferon α, β or γ or IL-2).

When the combination partners employed in the combinations as disclosed herein are applied in the form as marketed as single drugs, their dosage and mode of administration can take place in accordance with the information provided on the package insert of the respective marketed drug in order to result in the beneficial effect described herein, if not mentioned herein otherwise.

One embodiment of the invention includes combination and compositions as described herein wherein the compounds are used sequentially or simultaneously.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The compositions may, where appropriate, be conveniently presented in discrete dosage units and may be prepared by any of the methods well known in the art of pharmacy. All methods include the step of bringing into association the active with liquid carriers or finely divided solid carriers or both and then, if necessary, shaping the product into the desired composition The compounds may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds or combinations may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds or combinations are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds or combinations may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

It will be appreciated that the amount of the further agent required for use in treatment will vary not only with the particular compound selected but also with the route of administration, the nature of the condition for which treatment is required and the age and condition of the patient and will be ultimately at the discretion of the attendant physician. In general however a suitable dose will be in the range of from about 0.1 to about 750 mg/kg of body weight per day, for example, in the range of 0.5 to 60 mg/kg/day, or, for example, in the range of 1 to 20 mg/kg/day. The other agent is conveniently administered in unit dosage form; for example containing 5 to 2000 mg, 10 to 1500 mg, conveniently 20 to 1000 mg, most conveniently 50 to 700 mg of active ingredient per unit dosage form.

The present invention will be more readily understood by referring to the following example. The examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, the following methods and materials are described. The issued patents, published patent applications, and references that are cited herein are hereby incorporated by reference to the same extent as if each was specifically and individually indicated to be incorporated by reference. In the case of inconsistencies, the present disclosure will prevail.

EXAMPLES AND RESULTS

Unless indicated otherwise, all experiments are conducted with pentamidine bis(2-hydroxyethanesulfonate)

PO means: by mouth or oral

IV means: intravenous

Example 1: Pharmacokinetics of Pentamidine Following IV and PO Administration Female Fox Chase SCID CB17 Mice (average animal weight of 0.025 kg).

Pharmacokinetic and bioavailability (F): IV administration of 5 mg/kg versus PO administration of 50 mg/kg (pentamidine). Results in mice show a low bioavailability (F) of about 1% (FIG. 1).

Figure 2:
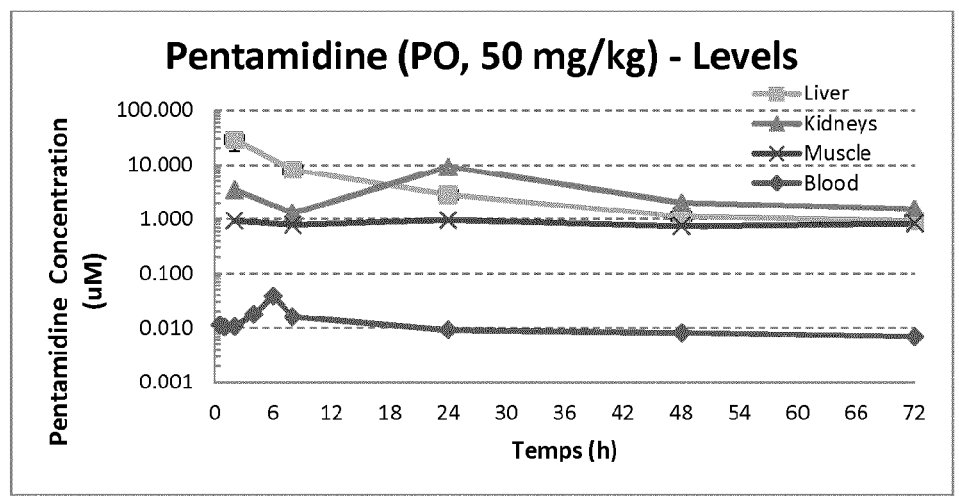
FIG. 2 represents the pentamidine levels following PO administration in liver, kidneys and muscle tissue.

Oral administration (PO) of 50 mg/kg of pentamidine using DMSO (5%) and sodium caprate (2%) suspension provided significant concentrations of pentamidine in tissues. Liver and kidney levels are significant after PO administration, and are several folds that of blood. Tissues like muscles also contain several folds the concentration found in blood. This result indicates that pentamidine is absorbed significantly in mice when administered orally. (FIG. 2)

Example 2: Repeated Oral Administration in Female Fox Chase SCID CB17 Mice (Average Animal Weight of 0.025 kg)

In this experiment, mice from all groups were first injected with pentamidine via the IV route on Day 1 (5 mg/kg). Tissue concentrations were assessed 24 hours later (on Day 2), and weekly thereafter (Day 7 and 14) with no subsequent pentamidine administration. Starting on Day 2, groups 2 and 3 were given pentamidine once a day (QD) or twice a day (BID) respectively and tissue levels were measured 24 hours later (Day 3) and weekly thereafter for two weeks.

Figure 3:
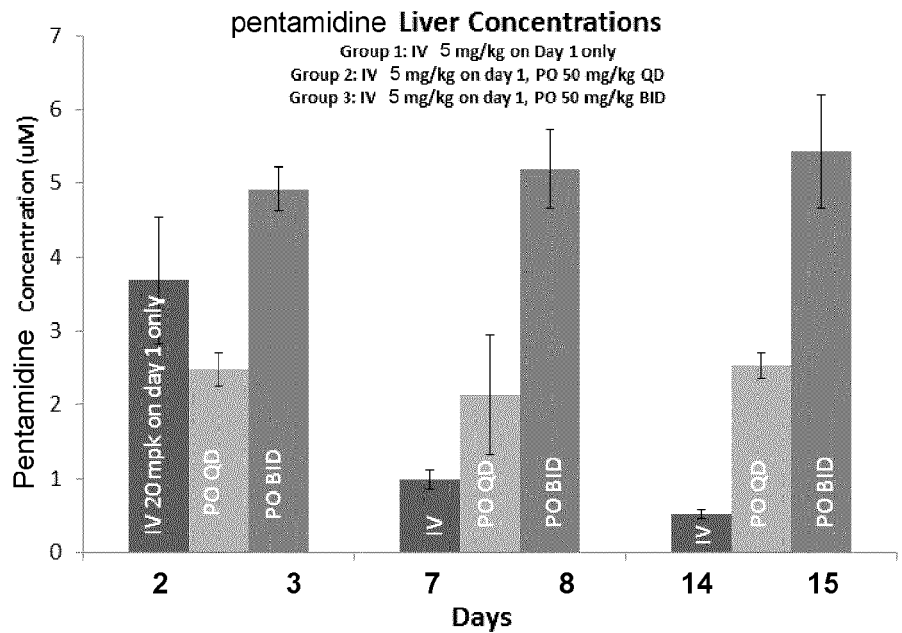
FIG. 3 represents the pentamidine mice liver concentrations following different dosage regimen (IV only versus IV followed by PO).

Results indicate clearly that it is possible to target the liver using the oral administration route. Pentamidine is clearly absorbed and liver concentrations can be maintained to a desired concentration depending on the oral administration regimen (e.g. QD and BID) (FIG. 3).

Kidney is targeted by IV administration, and very little by oral administration. Kidney levels are not affected by oral administration, indicating lower systemic exposure. The same is true for lungs and muscles, which all point to good oral bioavailability and high first pass extraction by liver following oral absorption.

Figure 4:
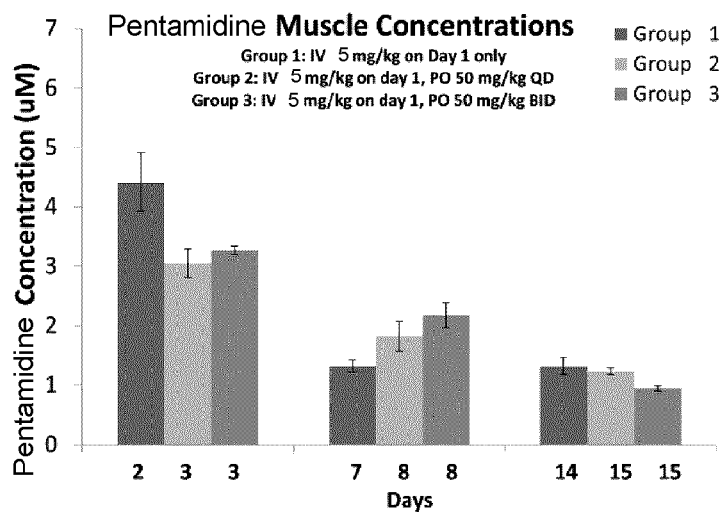
FIG. 4 represents the pentamidine mice muscle concentrations following different dosage regimen (IV only versus IV followed by PO).
Figure 5:
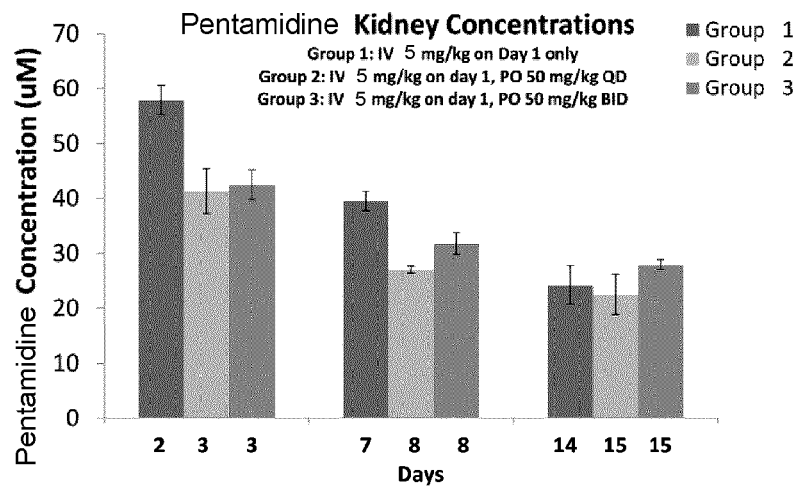
FIG. 5 represents the pentamidine mice kidney concentrations following different dosage regimen (IV only versus IV followed by PO).
Figure 6:
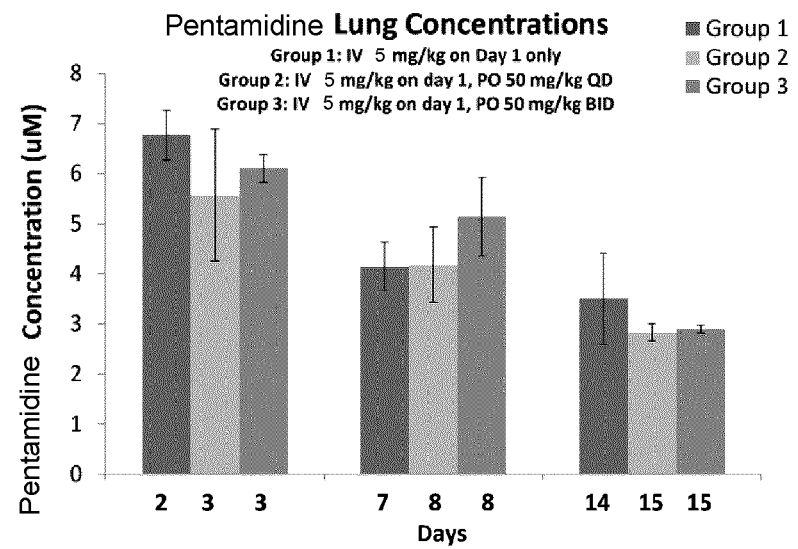
FIG. 6 represents the pentamidine mice lung concentrations following different dosage regimen (IV only versus IV followed by PO).

Pentamidine concentrations in other tissues (Kidneys, Lung and muscle) are not affected by the oral administration as much as the liver. This is visible by the similar pentamidine concentration decrease over time following the IV administration in all other tissues. There is no significant difference between groups, with or without PO administration, and with QD or BID PO administration (FIGS. 4, 5 and 6).

Example 3: A Repeat Dose Oral Capsule Administration or Intravenous Infusion Pharmacokinetics Study in Male Beagle Dogs. Three oral formulations were tested.

In this example, the pharmacokinetics and biodistribution are studied in Male Beagle Dogs. The Dog is a relevant model since the elimination rate from the different organs, mainly the liver, are closer to that observed in man. Three oral formulations were tested and compared to the injectable formulation:

PO2 capsules: this formulation utilizes Gelucire, Solutol and vitamin E TPGS as absorption enhancers or permeation enhancers. pentamidine/PEG400/Gelucire 44/14/Solutol HS 15/Vit. E. TPGS/SLS (19.5%/16.1%/32.2%/24.2%/4.0%/4.0%) dispersion;

PO3 capsules: Spray-Dried powder (70% pentamidine/30% PVP K30) with Sodium Caprate and L-Arginine as absorption or permeation enhancers.

PO4 capsules: This formulation does not contain any absorption or permeation enhancer. amorphous dispersion (spray-dried) of pentamidine/Glycerol/SLS (19.5%/76.4%/4.1%).

Pentamidine Spray-Dried formulation for PK study (Group PO2)

| | Item | Composition | |
|---|---|---|---|
| | | % w/w | mg/unit |
| a) | Spray-Dried Powder (composed of a1 and a2) | 75.4 | 307.0 |
| a1) | Pentamidine bis(2-hydroxyethanesulfonate) | 52.8 | 215.0 |
| a2) | PVP K30 | 22.6 | 92.0 |
| b) | Sodium caprate | 12.3 | 50.0 |
| c) | L-Arginine | 12.3 | 50.0 |
| d) | USP water* | 15.0 | — |
| e) | Ethanol* | 5.0 | — |
| | Fill weight: | 100.0 | 407.0 |
| g) | White Opaque HPMC capsule size "00" | — | 120.0 |
| | Total capsule weight: | — | 527.0 |

*Removed during processing, v/w (ml/g of solid)

PEG400 Pentamidine bis(2-hydroxyethanesulfonate) dispersion formulation for PK study (Group PO3)

| | Item | Composition | |
|---|---|---|---|
| | | % w/w | mg/unit |
| a) | Pentamidine bis(2-hydroxyethanesulfonate) | 19.5 | 215.0 |
| b) | PEG400 | 16.1 | 177.4 |
| c) | Gelucire 44/14 | 32.2 | 354.5 |

-continued

PEG400 Pentamidine bis(2-hydroxyethanesulfonate) dispersion formulation for PK study (Group PO3)

| | Item | Composition % w/w | mg/unit |
|---|---|---|---|
| d) | Solutol HS15 | 24.2 | 265.8 |
| e) | Vitamin E TPGS | 4.0 | 43.7 |
| f) | Sodium Lauryl Sulfate | 4.0 | 43.7 |
| | Fill weight: | 100.0 | 1100 |
| g) | White Opaque HPMC capsule size "00" | — | 120.0 |
| | Total capsule weight: | — | 1220.0 |

: Glycerol-based amorphous Pentamidine bis(2-hydroxyethanesulfonate) dispersion formulation (Group PO4)

| | Item | Composition % w/w | mg/unit |
|---|---|---|---|
| a) | Pentamidine bis(2-hydroxyethanesulfonate) | 19.5 | 215.0 |
| b) | Glycerol | 76.4 | 840.0 |
| c) | Sodium Lauryl Sulfate | 4.1 | 45.0 |
| | Fill weight: | 100.0 | 1100 |
| g) | White Opaque HPMC capsule size "00" | — | 120.0 |
| | Total capsule weight: | — | 1220.0 |

Experimental Design

The test item was administered twice daily by oral capsule administration for 3 days or once daily by 2-hour peripheral intravenous infusion for 2 days, as shown below:

| Treatment Group | Dose Route | Dose Level[e] (mg/kg/day) | Dose Conc. (mg/mL) | Dose Volume (mL/kg) | Infusion Rate (mL/kg/hr) | Number of Males |
|---|---|---|---|---|---|---|
| 1. Pent.-OS Formulation IV | IV[a] | 4 | 1 | 4 | 2 | 6[c] |
| 2. Pent.-OS Formulation PO2 | Oral capsules[b] | 35[e] | N/A | N/A | N/A | 3[d] |
| 3. pent.-OS Formulation PO3 | Oral capsules[b] | 35[e] | N/A | N/A | N/A | 3[d] |
| 4. pent.-OS Formulation PO4 | Oral capsules[b] | 35[e] | N/A | N/A | N/A | 3[d] |

[a]2-hour peripheral intravenous infusion once daily for 2 days.
[b]Twice daily (12 hours apart) oral capsule administration for 3 days.
[d]Necropsy/last sample collection from all animals at the following time-point relative to Day 1: 72 hours post-first dose.
[e]All doses reported in pent.-OS salt form equivalent (1.74 mg salt for 1 mg freebase). Capsules are administered at a fixed dose (420 mg/animal/occasion, based on target average weight of animals of 12 kg, 35 mg/kg/occasion).
N/A: not applicable Administration of Dosing Formulations Group 1 (IV Infusion):

The test item dosing formulation was administered once daily as a 2-hour intravenous infusion via the saphenous and/or cephalic vein using an infusion pump, using a temporary peripheral vein catheter attached to a syringe, for 2 consecutive days. The dose volume was 4 mL/kg and the infusion rate was 2 mL/kg/hour for all animals. The actual volume administered to each animal was calculated and adjusted based on the most recent practical body weight of each animal. The catheter was flushed with 0.9% Sodium Chloride for Injection, USP (saline) in order to ensure that the whole intended dose was administered to the animals, after which the temporary catheter was removed and discarded.

For dosing accountability purposes, the weight of the infusion syringes during the administration period was recorded prior to the start and following the end of each administration. The animals were restrained on a sling during each 2-hour dosing occasion.

Groups PO2, 3, and 4 (Oral Capsule Administration):

The test item was administered twice daily (targeted time: 12 hours apart) by oral capsule administration for 3 consecutive days to fasted animals (at least 4 hours prior to dosing). Food was returned 2 hours post-dose.

The number of capsules to be administered to each animal was fixed to 2 capsules/animals/occasion. If needed, following dosing, the oral cavity was rinsed with an appropriate volume of reverse osmosis water to facilitate swallowing. The oral cavity was inspected following dosing to ensure that the capsules have been swallowed.

Results

There was no significant difference between the three formulations in terms of pharmacokinetics and bioavailability (F). The average bioavailability was 0.4% when calculated using the AUC of the PO versus IV groups. This low apparent bioavailability hides a significant absorption of the drug, targeted in the liver (FIGS. 7 and 8).

Figure 7:
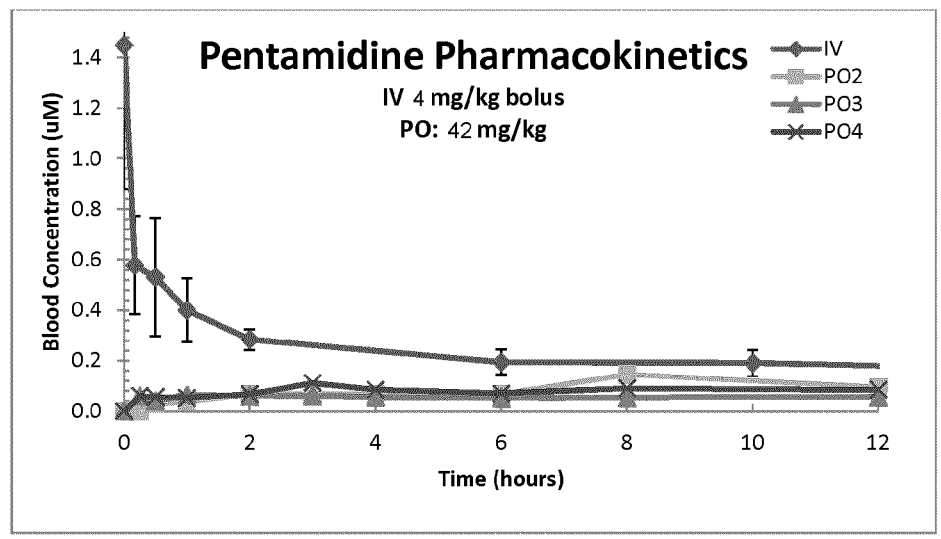
FIG. 7 represents the pharmacokinetics of pentamidine in dogs depending on the dosage regimen.
Figure 8:
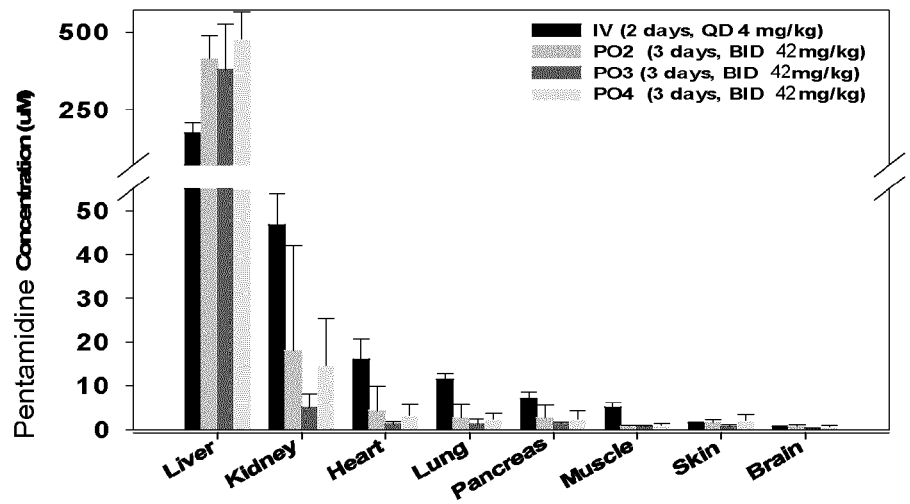
FIG. 8 represents the pentamidine tissue distribution following different dosage regimen (IV for two days versus PO for three days).

As can be seen in FIGS. 7 and 8, the oral absorption of pentamidine is predominantly in the liver, and much less in other organs and tissue compared to the IV absorption which distributes predominantly in the liver, but with much higher concentrations in other organs. In comparison, the oral absorption is clearly targeted to the liver.

The following tables present the different Pharmacokinetic parameters for IV and PO groups, the concentrations of pentamidine in different tissues and the tissue to blood and tissue to liver concentration ratios. These data also demonstrate the targeted delivery to the liver. pentamidine systemic exposure, to the blood compartment and other tissues, is significantly reduced to the profit of the targeted organ.

TABLE I

Pharmacokinetic Parameters of pentamidine in blood following 2-h IV administration in Beagle Dogs- Day 1

| Animal_ID | Cmax (umol/L) | Tmax (hr) | AUClast (hr * umol/L) | Tlast (h) | AUCINF (hr * umol/L) | AUC % Extrap (%) | $t_{1/2}$ (hr) | CL (L/hr/kg) | Vz (L/kg) | MRTlast (hr) |
|---|---|---|---|---|---|---|---|---|---|---|
| 1001 | 2.16 | 2 | 7.35 | 24 | 9.09 | 19.13 | NC | 1.29 | 18.59 | 6.36 |
| 1002 | 1.74 | 1 | 10.74 | 48 | 20.95 | 48.74 | NC | 0.56 | 22.93 | 18.84 |
| 1003 | 1.22 | 1 | 19.73 | 72 | 35.1 | 43.8 | NC | 0.34 | 32.19 | 30.73 |
| 1004 | 1.04 | 1 | 14.33 | 96 | 17.89 | 19.89 | 35.23 | 0.66 | 33.41 | 38.14 |
| 1005 | 1.43 | 1 | 19.11 | 120 | 24.54 | 22.12 | 47.05 | 0.48 | 32.52 | 45.29 |
| 1006 | 2.2 | 2 | 29.35 | 168 | 35.82 | 18.04 | NC | 0.33 | 26.52 | 65.59 |
| Mean | 1.632 | 1.333 | 16.769 | 88 | 23.898 | 28.619 | 41.14 | 0.609 | 27.694 | 34.156 |
| SD | 0.485 | 0.516 | 7.793 | 51.85 | 10.317 | 13.823 | 21.57 | 0.359 | 6.054 | 20.722 |
| CV % | 29.7 | 38.7 | 46.5 | 58.92 | 43.2 | 48.3 | 52.43 | 59 | 21.9 | 60.7 |

TABLE II

Pharmacokinetic Parameters of pentamidine in blood following PO administration in Beagle Dogs- Day 1

| | Animal_ID | Cmax (umol/L) | Tmax (hr) | AUClast (hr * umol/L) |
|---|---|---|---|---|
| Group 2 | 2001 | 0.04 | 4 | 0.26 |
| | 2002 | 0.23 | 8 | 1.55 |
| | 2003 | 0.06 | 8 | 0.53 |
| | Mean | 0.11 | 6.667 | 0.778 |
| | SD | 0.104 | 2.309 | 0.681 |
| | CV % | 94.9 | 34.6 | 87.5 |
| Group 3 | 3001 | 0.09 | 0.25 | 0.46 |
| | 3002 | 0.13 | 1 | 1.1 |
| | 3003 | 0.06 | 2 | 0.41 |
| | Mean | 0.093 | 1.083 | 0.655 |
| | SD | 0.035 | 0.878 | 0.39 |
| | CV % | 37.6 | 81 | 59.5 |
| Group 4 | 4001 | 0.06 | 4 | 0.62 |
| | 4002 | 0.09 | 8 | 0.78 |
| | 4003 | 0.22 | 3 | 1.44 |
| | Mean | 0.123 | 5 | 0.945 |
| | SD | 0.085 | 2.646 | 0.432 |
| | CV % | 69 | 52.9 | 45.7 |

TABLE III

Pharmacokinetic Parameters of pentamidine in blood following PO administration in Beagle Dogs- Day 3

| | Animal_ID | Cmax (umol/L) | Tmax (hr) | AUClast (hr * umol/L) | AUC TAU (hr * umol/L) | Accumulation Index |
|---|---|---|---|---|---|---|
| Group 2 | 2001 | 0.09 | 8 | 2.2 | 0.94 | NC |
| | 2003 | 0.2 | 12 | 2.91 | 1.23 | NC |
| | Mean | 0.145 | 10 | 2.554 | 1.084 | NA |
| | SD | 0.078 | 2.828 | 0.496 | 0.199 | NA |
| | CV % | 53.6 | 28.3 | 19.4 | 18.3 | NA |
| Group 3 | 3001 | 0.12 | 12 | 2.43 | 1.05 | NC |
| | 3002 | 0.34 | 12 | 4.23 | 1.65 | NC |
| | 3003 | 0.13 | 2 | 2.28 | 1.32 | 3.9 |
| | Mean | 0.197 | 8.667 | 2.982 | 1.342 | 3.896 |
| | SD | 0.124 | 5.774 | 1.087 | 0.303 | NA |
| | CV % | 63.2 | 66.6 | 36.4 | 22.6 | NA |
| Group 4 | 4001 | 0.21 | 8 | 3.85 | 1.81 | 16.7 |
| | 4002 | 0.22 | 1 | 4.68 | 2.52 | 3.87 |
| | 4003 | 0.14 | 12 | 2.43 | 1.11 | NC |
| | Mean | 0.19 | 7 | 3.655 | 1.815 | 10.286 |
| | SD | 0.044 | 5.568 | 1.138 | 0.705 | 9.069 |
| | CV % | 22.9 | 79.5 | 31.1 | 38.8 | 88.2 |

TABLE IV

Pharmacokinetic Parameters of pentamidine in tissues- IV dosing Day 1

| Organ | Cmax (umol/L) | Tmax (hr) | AUClast (hr * umol/L) |
|---|---|---|---|
| Liver | 210 | 168 | 27072 |
| Lung | 13.4 | 120 | 1807.2 |
| Muscle | 6.1 | 168 | 786 |
| Skin | 1.8 | 168 | 235.2 |

TABLE V

Summary of Tissue-to-Blood Ratios

| | Tissue-to-blood ratio | | | | | | | |
|---|---|---|---|---|---|---|---|---|
| | Lung | Skin | Muscle | Heart | Kidney | Pancreas | Brain | Liver |
| Group 1 | 61.57* | 26.78* | 8.01* | NC | NC | NC | NC | 922.38* |
| | 110.56 (45.98) | 14.44 (41.19) | 48.69 (51.67) | 132.92 (27.7) | 386.22 (15.15) | 58.40 (21.39) | 6.19 (18.37) | 1694.98 (48.41) |
| Group 2 | 7.48 (79.19) | 14.24 (58.08) | 6.68 (58.42) | 11.49 (60.99) | 39.18 (57.89) | 11.59 (70.38) | 4.18 (58.65) | 3836.52 (64.51) |
| Group 3 | 12.40 (103.35) | 7.30 (69.26) | 7.71 (32.85) | 13.16 (60.74) | 57.02 (63.30) | 13.37 (22.14) | 4.06 (29.20) | 4195.16 (44.01) |
| Group 4 | 16.96 (28.9) | 14.73 (32.31) | 7.65 (21.38) | 22 (69.89) | 99.4 (62.26) | 15.61 (50.76) | 4.06 (33.47) | 3735.13 (27.87) |

TABLE VI

Summary of Tissue-to-Liver

| | Tissue-to-Liver (%) | | | | | | |
|---|---|---|---|---|---|---|---|
| | Lung | Skin | Muscle | Heart | Kidney | Pancreas | Brain |
| Group 1 | 6.67* | 0.87* | 2.9* | | | | |
| | 6.74 (18.31) | 0.91 (25.4) | 2.9 (15.11) | 9.66 (56.37) | 28.4 (51.40) | 4.34 (61.27) | 0.46 (64.41) |
| Group 2 | 0.25 (92.12) | 0.41 (67.26) | 0.18 (61.23) | 0.31 (58.54) | 1.13 (66.34) | 0.29 (59.17) | 0.12 (69.11) |
| Group 3 | 0.19 (84.8) | 0.11 (57.74) | 0.20 (61.78) | 0.31 (21.69) | 1.26 (27.98) | 0.37 (58.33) | 0.10 (24.59) |
| Group 4 | 0.42 (67.69) | 0.51 (72.5) | 0.19 (58.8) | 0.63 (67.22) | 2.86 (61.85) | 0.48 (74) | 0.12 (55.19) |

*Based on AUC

Table VIIa, b and c—Individual Data—Tissue Concentrations and Ratios—Intravenous Dosing

TABLE VIIa

| | Concentrations (μmol/L) | | | | | | | | |
|---|---|---|---|---|---|---|---|---|---|
| | Blood | Liver | Lung | Skin | Muscle | Heart | Kidney | Pancreas | Brain |
| 1001 | 0.121 | 125 | 9.80 | 1.63 | 2.82 | 10.10 | 44.80 | 4.60 | 0.50 |
| 1002 | 0.25 | 159 | 11.80 | 1.63 | 5.56 | 14.20 | 39.70 | 7.10 | 0.80 |
| 1003 | 0.16 | 208 | 11.56 | 1.45 | 5.28 | 22.30 | 53.10 | 8.50 | 0.80 |
| 1004 | 0.07 | 174 | 11.52 | 1.23 | 4.98 | 13.90 | 38.30 | 6.00 | 0.80 |
| 1005 | 0.08 | 168 | 13.39 | 1.41 | 5.29 | 15.80 | 48.70 | 8.00 | 0.70 |
| 1006 | 0.08 | 210 | 10.48 | 1.80 | 6.11 | 20.20 | 55.80 | 8.20 | 0.90 |
| Mean | 0.13 | 173.82 | 11.42 | 1.52 | 5.01 | 16.08 | 46.73 | 7.07 | 0.75 |
| SD | 0.07 | 31.95 | 1.23 | 0.20 | 1.14 | 4.47 | 7.08 | 1.51 | 0.14 |
| % CV | 54.53 | 18.38 | 10.78 | 13.33 | 22.71 | 27.78 | 15.16 | 21.40 | 18.38 |

TABLE VIIb

| Tissue-to-blood ratio | | | | | | | |
|---|---|---|---|---|---|---|---|
| Liver | Lung | Skin | Muscle | Heart | Kidney | Pancreas | Brain |
| 1029 | 80.95 | 13.46 | 23.29 | 83.47 | 370.25 | 38.02 | 4.13 |
| 636 | 47.20 | 6.51 | 22.24 | 117.36 | 328.10 | 58.68 | 6.61 |
| 1297 | 72.23 | 9.09 | 32.98 | 184.30 | 438.84 | 70.25 | 6.61 |
| 2480 | 164.50 | 17.52 | 71.17 | 114.88 | 316.53 | 49.59 | 6.61 |
| 2105 | 167.42 | 17.56 | 66.15 | 130.58 | 402.48 | 66.12 | 5.79 |
| 2622 | 131.05 | 22.52 | 76.33 | 166.94 | 461.16 | 67.77 | 7.44 |
| 1694.99 | 110.56 | 14.44 | 48.69 | 132.92 | 386.23 | 58.40 | 6.20 |
| 820.58 | 50.84 | 5.95 | 25.16 | 36.92 | 58.55 | 12.50 | 1.14 |
| 48.41 | 45.98 | 41.19 | 51.68 | 27.78 | 15.16 | 21.40 | 18.38 |

TABLE VIIc

| Tissue-to-Liver (%) | | | | | | |
|---|---|---|---|---|---|---|
| Lung | Skin | Muscle | Heart | Kidney | Pancreas | Brain |
| 7.87 | 1.31 | 2.26 | 8.11 | 35.97 | 3.69 | 0.40 |
| 7.42 | 1.02 | 3.49 | 18.44 | 51.56 | 9.22 | 1.04 |
| 5.57 | 0.70 | 2.54 | 14.21 | 33.84 | 5.42 | 0.51 |
| 6.63 | 0.71 | 2.87 | 4.63 | 12.76 | 2.00 | 0.27 |
| 7.95 | 0.83 | 3.14 | 6.20 | 19.12 | 3.14 | 0.27 |

TABLE VIIc-continued

| Tissue-to-Liver (%) | | | | | | |
|---|---|---|---|---|---|---|
| Lung | Skin | Muscle | Heart | Kidney | Pancreas | Brain |
| 5.00 | 0.86 | 2.91 | 6.37 | 17.59 | 2.58 | 0.28 |
| 6.74 | 0.91 | 2.87 | 9.66 | 28.47 | 4.34 | 0.46 |
| 1.23 | 0.23 | 0.43 | 5.45 | 14.63 | 2.66 | 0.30 |
| 18.31 | 25.40 | 15.11 | 56.37 | 51.40 | 61.27 | 64.41 |

Table VIIIa, b- and c Individual Data—Tissue Concentrations and Ratios—Oral Dosing

TABLE VIIIa

| | | | 24 h post-dose | | | | | | |
|---|---|---|---|---|---|---|---|---|---|
| | Blood | Liver | Lung (μmol/L) | Skin | Muscle | Heart | Kidney | Pancreas | Brain |
| 2001 | 0.13 | 355.21 | 1.50 | 1.97 | 0.79 | 1.2 | 5.3 | 0.9 | 0.6 |
| 2002 | NC | 496.68 | 6.05 | 2.16 | 0.93 | 10.6 | 45.80 | 6.00 | 1.20 |
| 2003 | 0.08 | 395.25 | 0.27 | 1.07 | 0.58 | 1.1 | 3.00 | 1.30 | 0.30 |
| Mean | 0.11 | 415.71 | 2.61 | 1.73 | 0.77 | 4.30 | 18.04 | 2.73 | 0.70 |
| SD | 0.07 | 72.92 | 3.04 | 0.58 | 0.17 | 5.46 | 24.07 | 2.84 | 0.46 |
| % CV | 62.45 | 17.54 | 116.70 | 33.65 | 22.58 | 126.89 | 133.45 | 103.76 | 65.47 |
| 3001 | 0.11 | 256.63 | 0.79 | NC | 0.64 | 0.80 | 2.2 | 1.6 | 0.3 |
| 3002 | 0.09 | 542.31 | 2.43 | 0.91 | 0.95 | 2.00 | 8.30 | 1.40 | 0.40 |
| 3003 | 0.08 | 338.15 | 0.24 | 0.36 | 0.54 | 0.80 | 4.70 | 0.80 | 0.40 |
| Mean | 0.09 | 379.03 | 1.15 | 0.63 | 0.71 | 1.20 | 5.07 | 1.27 | 0.37 |
| SD | 0.02 | 147.16 | 1.14 | 0.46 | 0.22 | 0.69 | 3.06 | 0.42 | 0.06 |
| % CV | 16.37 | 38.83 | 98.72 | 72.08 | 30.40 | 57.74 | 60.38 | 32.87 | 15.75 |
| 4001 | 0.18 | 484.60 | 2.77 | 3.58 | 1.04 | 3.00 | 15.2 | 4.2 | 0.9 |
| 4002 | 0.15 | 560.75 | 3.37 | 1.58 | 1.34 | 5.90 | 25.10 | 2.40 | 0.70 |
| 4003 | 0.08 | 381.99 | 1.04 | 1.10 | 0.66 | 0.80 | 3.70 | 0.60 | 0.20 |
| Mean | 0.14 | 475.78 | 2.39 | 2.09 | 1.01 | 3.23 | 14.68 | 2.40 | 0.60 |
| SD | 0.05 | 89.71 | 1.21 | 1.32 | 0.34 | 2.56 | 10.71 | 1.80 | 0.36 |
| % CV | 37.55 | 18.85 | 50.45 | 63.05 | 33.70 | 79.11 | 72.98 | 75.00 | 60.09 |

TABLE VIIIb

| Tissue-to-blood ratio | | | | | | | |
|---|---|---|---|---|---|---|---|
| Liver | Lung | Skin | Muscle | Heart | Kidney | Pancreas | Brain |
| 2732.39 | 11.53 | 15.15 | 6.08 | 9.23 | 40.87 | 6.92 | 4.62 |
| NC | NC | NC | NC | NC | NC | NC | NC |
| 4940.66 | 3.43 | 13.33 | 7.27 | 13.75 | 37.50 | 16.25 | 3.75 |
| 3836.52 | 7.48 | 14.24 | 6.68 | 11.49 | 39.18 | 11.59 | 4.18 |
| 2474.96 | 5.92 | 8.27 | 3.90 | 7.01 | 22.69 | 8.15 | 2.45 |
| 64.51 | 79.19 | 58.08 | 58.42 | 60.99 | 57.89 | 70.38 | 58.65 |
| 2332.96 | 7.16 | NC | 5.81 | 7.27 | 20.10 | 14.55 | 2.73 |
| 6025.63 | 27.01 | 10.10 | 10.58 | 22.22 | 92.22 | 15.56 | 4.44 |
| 4226.89 | 3.03 | 4.51 | 6.73 | 10.00 | 58.75 | 10.00 | 5.00 |
| 4195.16 | 12.40 | 7.30 | 7.71 | 13.16 | 57.02 | 13.37 | 4.06 |
| 1846.54 | 12.82 | 5.06 | 2.53 | 7.96 | 36.09 | 2.96 | 1.18 |
| 44.02 | 103.35 | 69.26 | 32.85 | 60.47 | 63.30 | 22.14 | 29.20 |
| 2692.24 | 15.39 | 19.90 | 5.80 | 16.67 | 84.61 | 23.33 | 5.00 |
| 3738.33 | 22.46 | 10.53 | 8.92 | 39.33 | 167.33 | 16.00 | 4.67 |
| 4774.83 | 13.04 | 13.77 | 8.22 | 10.00 | 46.25 | 7.50 | 2.50 |
| 3735.13 | 16.96 | 14.73 | 7.65 | 22.00 | 99.40 | 15.61 | 4.06 |
| 1041.30 | 4.91 | 4.76 | 1.63 | 15.38 | 61.88 | 7.92 | 1.36 |
| 27.88 | 28.91 | 32.31 | 21.38 | 69.89 | 62.26 | 50.76 | 33.47 |

TABLE VIIIc

| Tissue-to-Liver (%) | | | | | | |
|---|---|---|---|---|---|---|
| Lung | Skin | Muscle | Heart | Kidney | Pancreas | Brain |
| 0.42 | 0.55 | 0.22 | 0.34 | 1.50 | 0.25 | 0.17 |
| NC | NC | NC | NC | NC | NC | NC |
| 0.07 | 0.27 | 0.15 | 0.28 | 0.76 | 0.33 | 0.08 |
| 0.25 | 0.41 | 0.18 | 0.31 | 1.13 | 0.29 | 0.12 |
| 0.23 | 0.28 | 0.11 | 0.18 | 0.75 | 0.17 | 0.08 |
| 92.12 | 67.26 | 61.23 | 58.54 | 66.34 | 59.17 | 69.11 |
| 0.31 | NC | 0.25 | 0.31 | 0.86 | 0.62 | 0.12 |
| NC | NC | NC | 0.37 | 1.53 | 0.26 | 0.07 |
| 0.07 | 0.11 | 0.16 | 0.24 | 1.39 | 0.24 | 0.12 |
| 0.19 | 0.11 | 0.20 | 0.31 | 1.26 | 0.37 | 0.10 |
| 0.16 | 0.06 | 0.13 | 0.07 | 0.35 | 0.22 | 0.03 |
| 84.80 | 57.74 | 61.78 | 21.69 | 27.98 | 58.33 | 24.59 |
| 0.57 | 0.74 | 0.22 | 0.62 | 3.14 | 0.87 | 0.19 |
| NC | NC | NC | 1.05 | 4.48 | 0.43 | 0.12 |
| 0.27 | 0.29 | 0.17 | 0.21 | 0.97 | 0.16 | 0.05 |
| 0.42 | 0.51 | 0.19 | 0.63 | 2.86 | 0.48 | 0.12 |
| 0.29 | 0.37 | 0.11 | 0.42 | 1.77 | 0.36 | 0.07 |
| 67.69 | 72.51 | 58.81 | 67.22 | 61.85 | 74.00 | 55.19 |

Example 4: A Repeat Dose Oral Tablet Administration or Intravenous Infusion

Determination of the pharmacokinetic profile and elimination of Pentamidine (Pentamidine isethionate), following repeat dose administration twice daily for 3 days by oral tablet or once daily (2-hour peripheral intravenous (IV) infusion) for 2 days by infusion to male Beagle dogs. The tissue elimination period studied in this example spans over 56 days. The tablet formulation tested in this example does not contain any absorption or permeation enhancer.

Experimental Design

PENTAMIDINE was administered twice daily by oral tablet administration for 3 days or once daily by 2-hour peripheral intravenous infusion for 2 days, as shown below:

| Treatment Group | Dose Route | Compound | Dose Level (mg/kg/day) | Dose Conc. (mg/mL) | Dose Volume (mL/kg) | Infusion Rate (mL/kg/hr) | Number of Males |
|---|---|---|---|---|---|---|---|
| 1. PENTAMIDINE-Formulation 1 | IV[a] | Pentamidine | 4 | 1 | 4 | 2 | 9[d] |
| 2. PENTAMIDINE Formulation 2 | Oral Tablet[b] | Negative control | N/A | N/A | N/A | N/A | 2[e] |
| 3. PENTAMIDINE Formulation 3 | Oral Tablet[b] | PO Pentamidine | 30[g] | N/A | N/A | N/A | 6[f] |

Figure 9:
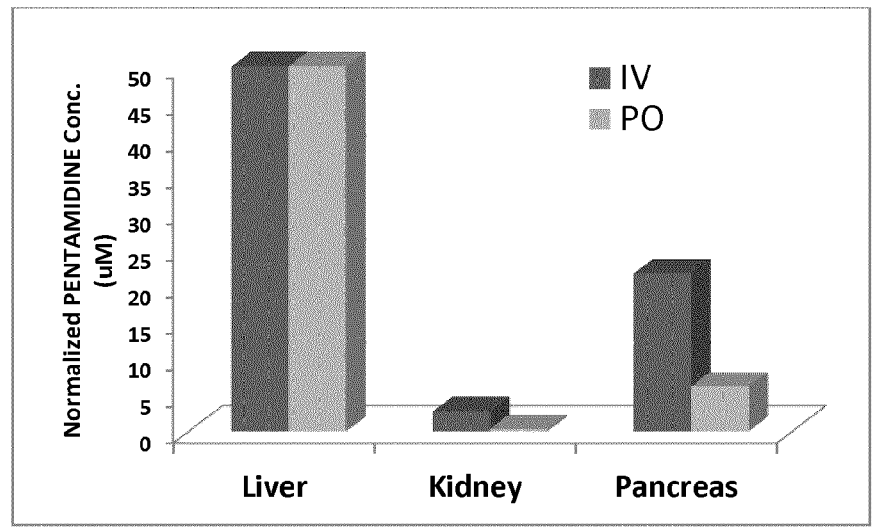
FIG. 9. Biodistribution Profiles 24 hours after last dose (Normalized for Equivalent Liver Concentrations of 50 uM): PENTAMIDINE (pentamidine) PO administration versus IV administration.

[a]2-hour peripheral intravenous infusion once daily for 2 days.
[b]Twice daily (12 hours apart) oral tablet for 3 days.
[d]Necropsy/last sample collection from 3 animals at each of the following time-points relative to Day 1: 14, 28 and 56 days post-dose.
[e]Necropsy/last sample collection from one animal at each of the following time-points relative to Day 1: 4 and 56 days post-dose.
[f]Necropsy/last sample collection from 3 animals at each of the following time-points relative to Day 1: 4 and 56 days post-dose.
[g]All doses reported in PENTAMIDINE salt form equivalent (1.74 mg salt for 1 mg freebase). Tablets will be administered at a fixed dose (1 × 210 mg/animal/occasion, based on target average weight of animals of 7 kg, 30 mg/kg/occasion).
N/A: not applicable Results Biodistribution of PENTAMIDINE in organs following PO administration using an instant-release tablet favored the liver, most likely by a first-pass extraction. By normalizing the liver concentrations, one can determine the key organ exposures endured from a PO administration versus an IV administration. As seen below and in FIG. 9, significantly lower exposure to the pancreas and kidney, known target organs of pentamidine IV, is observed.

Using the IV administration results of examples 3 and 4, it was possible to confirm the long liver elimination half-life in higher rank animals such as the dog. The elimination half-life from the liver is calculated to be approximately of 28 days, making possible the accumulation and maintenance of therapeutically active concentrations in the liver with minimal systemic exposure.

Example 5: GalN/LPS Fulminant Liver Injury: An Anti-Inflammatory, Anti-TNFα, Hepatoprotection Model To evaluate the anti-inflammatory, anti-TNFα and hepato-protective properties of PENTAMIDINE, a Galactosamine/Liposaccharide (GalN/LPS) fulminant liver injury model was used. In order to test the biological properties of PENTAMIDINE in a fulminant injury model such as the GalN/LPS, mice and therefore intraperitoneal administration (IP) knowing this would provide best drug exposure to the liver, and mimic as best possible the exposure that a dog or a man would have following oral administration.

Three independent experiments on mice untreated or pretreated with vehicle, compound PENTAMIDINE (isethionate salt) at doses of 25 and 40 mg/kg. PENTAMIDINE is dosed IP 30-minutes prior to the co-treatment with subtoxic doses of hepatotoxin GalN and immune stimulant LPS. Mice were sacrificed at 6.5 hours after GalN/LPS for analysis. The analysis of alanine transaminase (ALT) serum levels and histological observations allow the evaluation of the hepato-protective, anti-TNF-α, anti-inflammatory and/or anti-fibrotic activity.

Results

Figure 10:
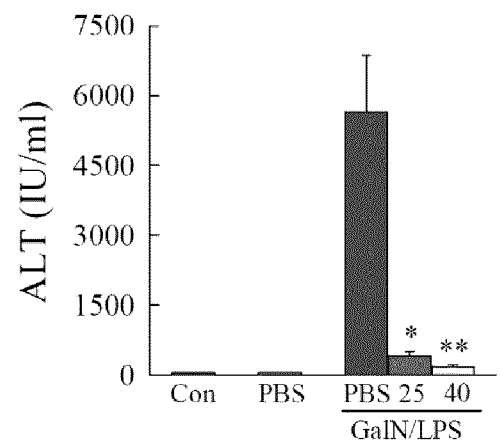
FIG. 10. Serum ALTs in uninjected control (Con) and PBS alone injected (PBS) mice, and mice GalN/LPS-treated and cotreated with PBS or PENTAMIDINE at 25 and 40 mg/kg (*P<0.006, **P<0.0005 as compared to PBS+GalN/LPS; n=3-7).
Figure 11:
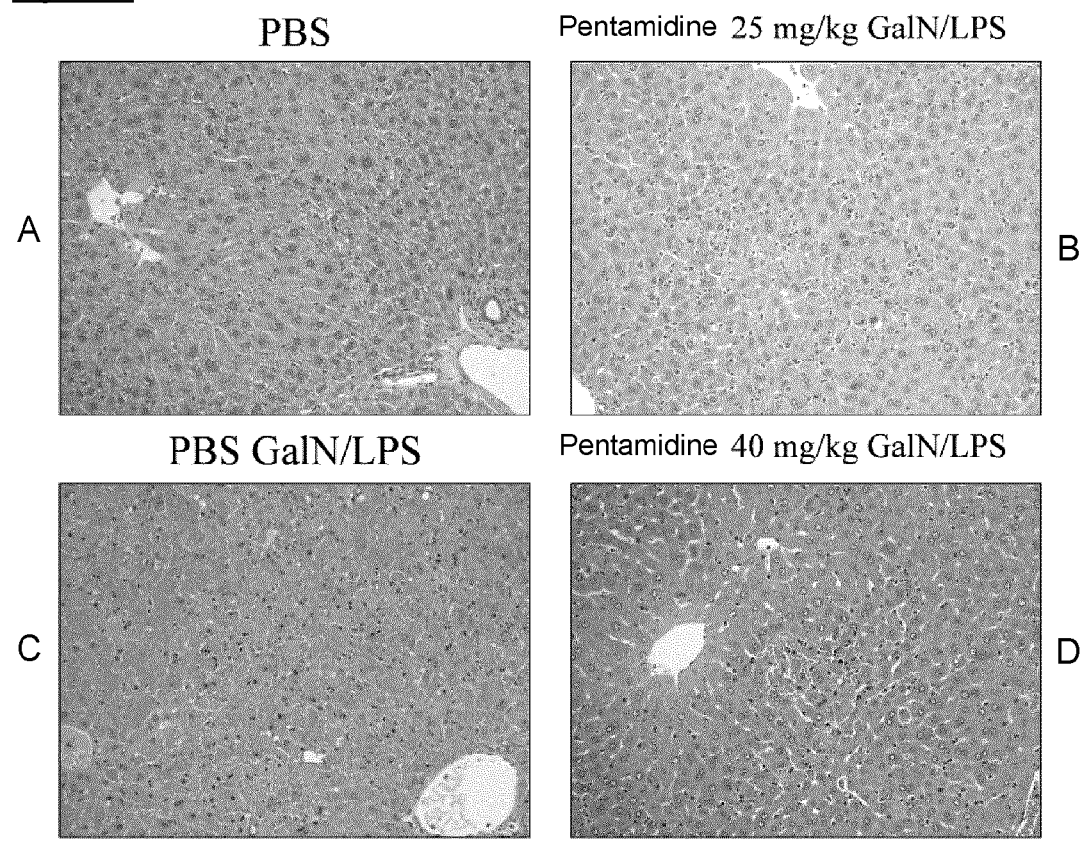
FIG. 11. Histology improvement for mice. ALT levels of mice following administration of nothing vehicle (PBS) (A), or GalN/LPS insult to the liver followed by treatment of with vehicle (PBS) (C), 25 or 40 mg/kg (B) (D) of PENTAMIDINE.
Figure 12:
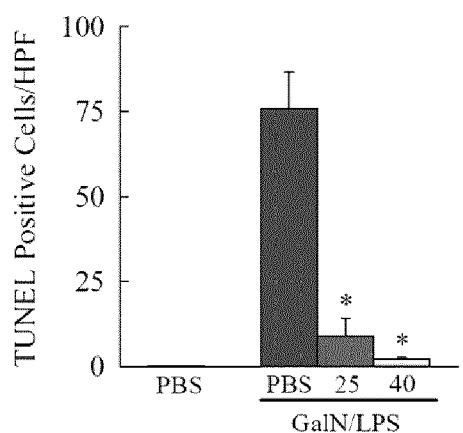
FIG. 12. Numbers of TUNEL-positive cells are significantly decreased by PENTAMIDINE. Numbers of TUNEL positive cells per high power field (HPF; 200x) in the livers of control and treated mice (*P<0.0002 as compared to PBS+GalN/LPS; n=6-7).

Serum ALT levels obtained following PENTAMIDINE IP administration of 25 mg/kg or 40 mg/kg are reduced 93% and 97% respectively relative to the treatment with the PBS vehicle. The results clearly indicate that PENTAMIDINE blocks liver injury (Results: PBS 5,632+/−1,223; PENTAMIDINE 25 mg/kg=402+/−105; PENTAMIDINE 40 mg/kg=177+/−44) (see FIG. 10-12).

Example 6: Pentamidine Salts in GalN/LPS Fulminant Liver Injury Model: An Anti-Inflammatory, Anti-TNFα, Hepatoprotection Model To evaluate the anti-inflammatory, anti-TNFα and hepato-protective properties of different pentamidine salt such as pentamidine bis-HCl (penta-HCL) and pentamidine tosylate (penta-Tos), a Galactosamine/Liposaccharide (GalN/LPS) fulminant liver injury model was used.

Pentamidine HCl and Tosylate were dosed IP 30-minutes prior to the co-treatment with subtoxic doses of hepatotoxin GalN and immune stimulant LPS. Mice were sacrificed at 6.5 hours after GalN/LPS for analysis. The analysis of alanine transaminase (ALT) serum levels and histological observations allow the evaluation of the hepato-protective, anti-TNF-α, anti-inflammatory and/or anti-fibrotic activity.

Results

Figure 13:
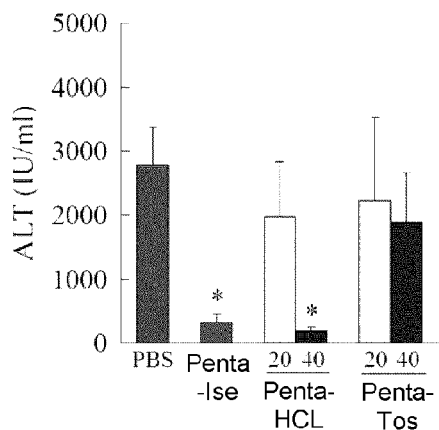
FIG. 13. Serum ALTs in mice pretreated with PBS, PENTAMIDINE isethionate 40 mg/kg, or penta-HCL and penta-Tos 20 and 40 mg/kg as indicated, and then administered GalN/LPS (*P<0.008 as compared to PBS+GalN/LPS; n=3-5).

Results indicate that pentamidine salts also possess the intrinsic activity (see FIG. 13).

Example 7: Oral Bioavailability of Pentamidine Salts

In this experiment, HCl, isethionate and tosylate salts of pentamidine were administered orally to mice and their PK and tissue accumulations were compared.

PK parameters for pentamidine salt following oral administration of 200 mg/kg in mice.

|  | Isethionate salt | HCl salt | Tosylate salt |
|---|---|---|---|
| Cmax (uM) | 3.06 | 5.24 | 0.43 |
| Tmax (hr) | 3.33 | 2.67 | 6.67 |
| AUCINF (uM * hr) | 23.0 | 158.1 | 17.8 |
| Cl/F (L/kg/hr) | 15.3 | 5.1 | 26.4 |
| Vz/F (L/kg) | 994 | 352 | 1464 |
| t½ (hr) | 44.5 | 90.8 | 54.9 |
| MRT (hr) | 52.8 | 136.0 | 86.0 |
| F* | 3.0 | 20.7 | 2.3 |

*Based on the iv AUC at 5 mg/kg of 19.08

Biodistribution of Pentamidine Salts in mice, 24 hours after PO administration of 200 mg/kg.

|  | | Tissue Concentration (uM) | | |
| --- | --- | --- | --- | --- |
| Salt | Kidney | Liver | Lung | Pancreas |
| Penta-Ise | Diisethionate | 5.0 | 5.6 | 2.7 | 1.3 |
| Penta-HCL | HCl | 156.3 | 224.6 | 43.4 | 16.6 |
| Penta-Tos | Tosylate | 1.9 | 4.1 | 0.5 | 0.5 |

Figure 14:
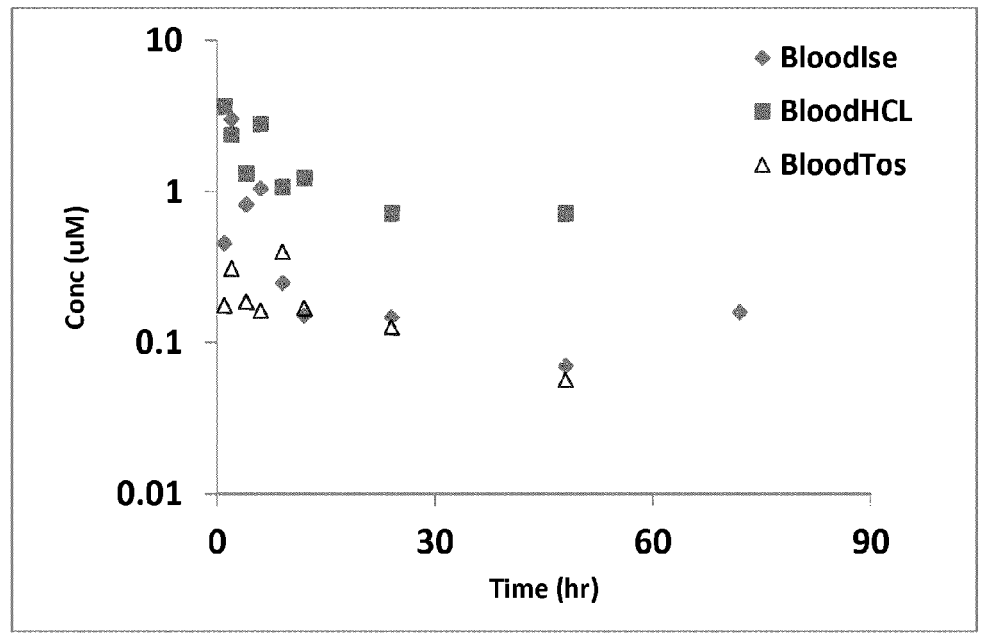
FIG. 14. Blood pentamidine PK profile after PO dose of 200 mg/kg in mice for isethionate salt (◇), HCl salt (□) and tosyate salt (Δ).

Different salts of pentamidine have different bioavailability, which may be affected by formulation and/or their intrinsic solubility. (see FIG. 14).

Example 8: Diabetic and High-Fat Diet Model

In this experiment, NASH-like pathology is induced in C57BL/6 mice by a single subcutaneous injection of 200 ug streptozotocin 2 days after birth and feeding with high fat diet (HFD, 57 kcal % fat, cat#: HFD32, CLEA Japan, Japan) after 4 weeks of age (STAM mice). Vehicle or pentamidine treatment was administered three times a week from 6 to 9 weeks of age. Vehicle (0.9% NaCl) and PENTAMIDINE were administered by intraperitoneal route in a volume of 10 mL/kg.

| Group | No. mice | Mice | Test article | Dose | Volume (mL/kg) | Regimens | Sacrifice (wks) |
| --- | --- | --- | --- | --- | --- | --- | --- |
| 1 | 6 | STAM | Vehicle | — | 10 | IP, three times a week, 6 wks-9 wks | 9 |
| 2 | 6 | STAM | PENTAMIDINE | 5 mg/kg | 10 | IP, three times a week, 6 wks-9 wks | 9 |
| 3 | 6 | STAM | PENTAMIDINE | 25 mg/kg | 10 | IP, three times a week, 6 wks-9 wks | 9 |

Figure 15:
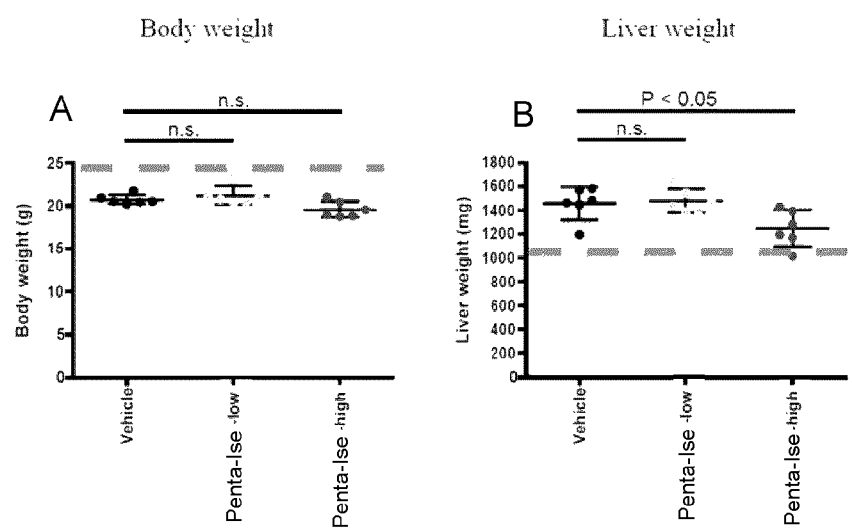
FIG. 15. Body weight (A) and Liver weight (B) for Mice Treated with Vehicle or with PENTAMIDINE. Dotted lines in the FIGS. 15A and 15B represent average values obtained by historical control.
Figure 16:
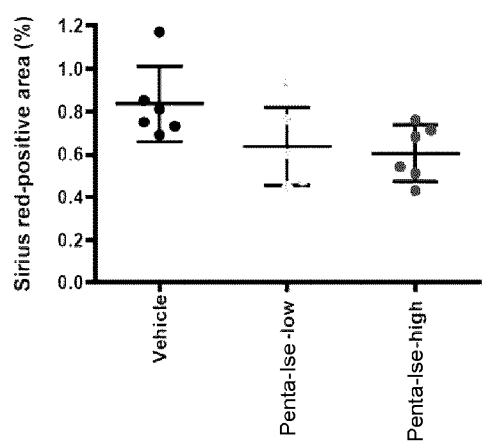
FIG. 16. Sirius Red Staining of Liver Treated with Vehicle or PENTAMIDINE.

Results:

Results obtained from this experiment indicate a trend for benefice of using PENTAMIDINE in the treatment of NASH. Liver weights of the high dose group was close to normal mice control values (FIG. 15) while fibrosis formation showed a trend for reduction in the PENTAMIDINE high dose group (FIG. 16).

Example 9: Aromatic Diamidines in GalN/LPS Fulminant Liver Injury Survival Study In this experiment, the 8-hour survival rate for C57BL/6 mice is evaluated when treated or not with two different aromatic diamidines (pentamidine isethionate (C5) and decamidine isethionate (C10)). Both compounds were administered intraperitoneally at doses close to their MTD 30 minutes prior a GalN/LPS-induced liver injury. Results indicate that aromatic diamidines have potential in hepatoprotection.

|  | 8-hour survival |
| --- | --- |
| PBS | 0% |
| PBS/GalN/LPS | 0% |
| PENTAMIDINE (40 mpk) | 83% |
| Decamidine (10 mpk) | 100% |

REFERENCES

1. Copaci I, Micu L, Voiculesciu M The Role of Cytokines in Non-Alcoholic Steatohepatitis: A Systematic Review. J Gastrointestin Liver Dis 2006; 15 (4):363-373
2. Quay J, Rosenthal G, Becker S. Effect of pentamidine on cytokine (IL-1 beta, TNF alpha, IL-6) production by human alveolar macrophages in vitro. Exp Lung Res. 1993 July-August; 19(4):429-43.
3. Van Wauwe J, Aerts F, Van Genechten H, Blockx H, Deleersnijder W, Walter H. The inhibitory effect of pentamidine on the production of chemotactic cytokines by in vitro stimulated human blood cells. Inflamm Res. 1996 July; 45(7):357-63.

The invention claimed is:

1. A method for reducing liver damage or liver injury following exposure to an hepatotoxin, comprising the step of orally administering a therapeutically effective amount of at least one diamidine analogue or a pharmaceutically acceptable salt thereof to a human patient in need thereof, wherein the diamidine analogue is pentamidine or decamidine or a pharmaceutically acceptable salt thereof.

2. The method of claim 1, wherein the diamidine analogue is pentamidine or a pharmaceutically acceptable salt thereof.

3. The method of claim 1, wherein the diamidine analogue is decamidine or a pharmaceutically acceptable salt thereof.

4. The method of claim 1, wherein the diamidine analogue is pentamidine bis(2-hydroxyethanesulfonate), pentamidine isethionate, pentamidine HCl or pentamidine tosylate.

5. The method of claim 4, wherein the diamidine analogue is pentamidine isethionate.

6. The method of claim 1, wherein the diamidine analogue is administered at least once daily at a dose of about 1 mg to about 3000 mg, of about 1 mg to about 2000 mg or of about 50 mg to about 700 mg.

7. The method of claim 1, wherein the diamidine analogue is administered for more than 15, 60, 120 or 365 consecutive days.

8. The method of claim 1, wherein the diamidine analogue is orally administered as a solid dosage form or as an instant release solid dosage form.

9. The method of claim 1, wherein the diamidine analogue is administered in combination with a further agent indicated for reducing liver damage or liver injury.

10. A method for reducing liver damage following exposure to an hepatotoxin, comprising the step of orally administering a therapeutically effective amount of pentamidine or a pharmaceutically acceptable salt thereof to a human patient in need thereof.

11. The method of claim 10, wherein pentamidine or a pharmaceutically acceptable salt thereof is pentamidine bis (2-hydroxyethanesulfonate), pentamidine isethionate, pentamidine HCl or pentamidine tosylate.

12. The method of claim 11, wherein pentamidine or a pharmaceutically acceptable salt thereof is pentamidine isethionate.

13. The method of claim 10, wherein pentamidine or a pharmaceutically acceptable salt thereof is administered at least once daily at a dose of about 50 mg to about 700 mg.

14. A method for reducing liver injury following exposure to an hepatotoxin, comprising the step of orally administering a therapeutically effective amount of pentamidine or a pharmaceutically acceptable salt thereof to a human patient in need thereof.

15. The method of claim 14, wherein pentamidine or a pharmaceutically acceptable salt thereof is pentamidine bis (2-hydroxyethanesulfonate), pentamidine isethionate, pentamidine HCl or pentamidine tosylate.

16. The method of claim 15, wherein pentamidine or a pharmaceutically acceptable salt thereof is pentamidine isethionate.

17. The method of claim 14, wherein pentamidine or a pharmaceutically acceptable salt thereof is administered at least once daily at a dose of about 50 mg to about 700 mg.

* * * * *